United States Patent
Haar et al.

(10) Patent No.: US 8,142,366 B2
(45) Date of Patent: Mar. 27, 2012

(54) ASSEMBLY FOR RECEIVING BODY FLUIDS, AND METHOD FOR THE PRODUCTION THEREOF

(75) Inventors: Hans-Peter Haar, Wiesloch (DE); Irio Giuseppe Calasso, Arth (CH); Otto Fuerst, Viernheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 535 days.

(21) Appl. No.: 12/037,197

(22) Filed: Feb. 26, 2008

(65) Prior Publication Data

US 2008/0200887 A1 Aug. 21, 2008

Related U.S. Application Data

(63) Continuation of application No. PCT/EP2006/008436, filed on Aug. 29, 2006.

(30) Foreign Application Priority Data

Sep. 1, 2005 (EP) .................................... 05019055

(51) Int. Cl.
*A61B 5/00* (2006.01)
*A61B 17/14* (2006.01)
*A61B 17/32* (2006.01)

(52) U.S. Cl. ........................................ 600/583; 606/181

(58) Field of Classification Search .......... 600/562–584; 606/167, 181–183

See application file for complete search history.

(56) References Cited

U.S. PATENT DOCUMENTS

| | | | |
|---|---|---|---|
| 6,988,996 B2 | 1/2006 | Roe et al. | |
| 7,604,604 B2 | 10/2009 | Roe | |
| 7,645,241 B2 | 1/2010 | Roe | |
| 2002/0188224 A1* | 12/2002 | Roe et al. | 600/584 |
| 2003/0018282 A1 | 1/2003 | Effenhauser et al. | |
| 2003/0028125 A1 | 2/2003 | Yuzhakov et al. | |
| 2003/0171699 A1 | 9/2003 | Brenneman | |
| 2004/0072357 A1 | 4/2004 | Stiene et al. | |
| 2006/0293611 A1 | 12/2006 | Calasso et al. | |
| 2007/0038149 A1 | 2/2007 | Calasso et al. | |
| 2008/0103415 A1 | 5/2008 | Roe et al. | |

FOREIGN PATENT DOCUMENTS

| | | |
|---|---|---|
| EP | 1 284 121 A2 | 2/2003 |
| EP | 1 360 933 B1 | 11/2003 |
| WO | WO 2004/066822 A2 | 8/2004 |
| WO | WO 2005/084530 A2 | 9/2005 |
| WO | WO 2005/084545 A1 | 9/2005 |
| WO | WO 2005/084546 A2 | 9/2005 |

OTHER PUBLICATIONS

International Patent Application No. PCT/EP2006/008436 International Search Report mailed Jan. 23, 2007.
English Translation of International Patent Application PCT/EP2006/008436 International Preliminary Report on Patentability mailed Apr. 8, 2008.

* cited by examiner

*Primary Examiner* — Jeffrey G Hoekstra
(74) *Attorney, Agent, or Firm* — Woodard, Emhardt, Moriarty, McNett & Henry LLP

(57) ABSTRACT

For an assembly for receiving body fluids comprising a sampling element (10) that has a collecting area (12) for collecting body fluid obtained by a puncture, it is proposed that the collecting area is formed by a longitudinal slot (12) which is elongated as a capillary that is open on both sides via side openings (28, 30) on the sampling element (10).

31 Claims, 4 Drawing Sheets

ASSEMBLY FOR RECEIVING BODY FLUIDS, AND METHOD FOR THE PRODUCTION THEREOF

CROSS-REFERENCE TO RELATED APPLICATIONS

This application is a continuation of International Application No. PCT/EP2006/008436, filed Aug. 29, 2006, published on Mar. 8, 2007 as WO 2007/025713 A1, which claims the benefit of European Application EP 05019055.2, filed Sep. 1, 2005, which are hereby incorporated by reference in their entirety.

BACKGROUND

The invention concerns an assembly or device for receiving body fluids such as blood comprising a sampling element preferably provided with a lancing member for insertion into a body part which has a collecting area for collecting body fluid obtained by a puncture, and comprising a sample receiving element to which body fluid can be applied via the collecting area and preferably provided with a test field for an analyte in the body fluid. The invention additionally concerns a process for producing such a sampling element.

An assembly for collecting body fluid for analytical purposes and in particular for determining blood glucose concentrations is described in an earlier application PCT/EP2005/002357 of the applicant. It describes a lancing element with a collecting zone for receiving body fluid where the collecting zone can be formed by lateral openings. Hence liquid can be transferred perpendicularly to the lancing direction onto a sampling element that is brought into fluidic contact thus avoiding a capillary transport over macroscopic paths with high dead volumes.

SUMMARY

On this basis the object of the invention is to further develop the known systems in the prior art and to optimize an assembly of the type stated above with respect to an improved sample uptake, where one object of the invention is also a simplified production.

The combination of features stated in the independent claims is proposed to achieve this object. Advantageous embodiments and further developments of the invention are derived from the dependent claims.

The invention is based on the idea of achieving a capillary sample uptake that is as reliable as possible by a capillary slot that is open on both sides. Accordingly it is proposed according to the invention that the collecting area is formed by a longitudinal slot which is elongated as a capillary and is open on both sides via side openings on the sampling element, wherein the longitudinal slot is separated from the sample receiving element in a collecting position of the sampling element so that no body fluid is transferred, and is in fluidic contact or fluidic connection with the sample receiving element in a transfer position of the sampling element. This ensures that sample can be rapidly taken up from both sides in a uniform volume whereby no active external action is necessary due to the capillary action. The slot runs particularly preferably in the longitudinal or lancing direction of a sampling element designed as a lancing element. However, it is also conceivable that a sample is taken up after producing a puncture by means of a separate lancing apparatus. In comparison to tubular or semi-open capillaries, the open slot design also further reduces the risk of blockages by tissue components. Furthermore, the subsequent sample handling can be substantially improved by the opening on two sides and it is possible to achieve a transfer that is substantially free of dead volume. The sample receiving element to which body fluid can be applied via the collecting area is preferably provided with a test field for an analyte in the body fluid to increase the degree of integration also with regard to the analysis. This enables a rapid transfer of liquid that is substantially free of loss onto the previously separated receiving element in order to allow the analysis to take place at a defined time.

According to a preferred embodiment of the invention the length of the longitudinal slot is such that the longitudinal slot is partially within and partially outside the body part in a collecting position of the sampling element. This allows the slot to be vented during the liquid uptake and an additional collecting volume is available. In this connection it is advantageous for the longitudinal slot to have a distal receiving section protruding into the skin of the body part and a proximal venting section located outside the skin when the body fluid is collected.

The longitudinal slot advantageously has a length of 0.5 to 4 mm, preferably of 1 to 2 mm and a width of less than 500 µm, preferably less than 100 µm. Furthermore, it is advantageous when the longitudinal slot is arranged at a distance of preferably about 50 to 200 µm from a distal tip of the sampling element which forms the lancing member.

In order to reduce the pain sensation during a puncture and at the same time to create an adequate receiving volume, the sampling element can have a distal shaft section with a tapered cross-section in the area of the longitudinal slot and a proximal shaft section with a widened cross-section.

In this connection another improvement is achieved by means of the fact that in the collecting position of the sampling element, the longitudinal slot is spatially and/or fluidically separated from the sample receiving element and, in a transfer position of the sampling element, is coupled with the sample receiving element to transfer body fluid via a side opening.

In this case it is also advantageous when, in a transfer position, the side opening of the longitudinal slot that is opposite to the outlet is connected to an actuator for the active transfer of body fluid onto the receiving element.

The actuator advantageously acts on the body fluid in the longitudinal slot by means of pneumatic and/or mechanical displacement means, in which case a mechanical actuator can be formed by a membrane that can be deformed against the longitudinal slot. It is also advantageous when the actuator has a compressed air passage that can be coupled to the side opening of the longitudinal slot that faces away from the sample receiving element.

In order for liquid to be transferred as completely as possible, it is advantageous when the sample receiving element has an at least comparable or larger capillary attraction for the body fluid than the longitudinal slot.

Another advantageous embodiment provides that the sampling element is movably mounted in a guide relative to the sample receiving element. For reasons of protection and hygiene it is advantageous in this connection when the sample receiving element forms a case which receives the sampling element.

Further handling advantages for the user can be achieved in that several sampling elements are stored in a first magazine and several sample receiving elements are stored in a second magazine, wherein the magazines as separate units can be connected together in order to couple the sampling elements and sample receiving elements in pairs.

An advantageous embodiment is that a plurality of sampling elements are arranged in a magazine and preferably in a drum magazine such that they can be ejected axially and that their associated sample receiving elements preferably arranged in push-through chambers are arranged in front of the magazine in the direction of ejection.

The invention also concerns a portable blood analyser for receiving at least one collecting assembly according to the invention preferably in the form of a single-use article.

The invention also concerns a system for analysing body fluids such as blood comprising a sampling element preferably provided with a lancing member for insertion into a body part which has a longitudinal slot elongated as a capillary that is open on both sides via side openings as a collecting area for collecting body fluid obtained by a puncture, and a sample receiving element to which body fluid can be applied via the collecting area and which is preferably provided with a test field for an analyte in the body fluid, wherein an actuator is provided for transferring body fluid from the sampling element onto the sample receiving element. In order to utilize the advantages of the slit openings on both sides in a particularly space saving manner, it is advantageous when the actuator acts from one side opening on the body fluid in the longitudinal slot and that an analyte in the body fluid is measured on the opposing side of the sampling element wherein, in a transfer position, the sampling element is in fluidic contact with the sample receiving element via the side opening facing away from the actuator. In such an instrument which preferably has disposable elements for liquid processing, a preferably optical measuring unit is provided to detect an analyte on the test field to which the body fluid has been applied.

With regard to the process the object mentioned above is achieved by using laser cutting to form a longitudinal slot in the sampling element that is open on both sides as a collecting area for the body fluid.

In this connection it is advantageous when the boundary surface of the longitudinal slot is hydrophilized during the laser cutting.

Another improvement provides that the laser energy and/or the speed of movement of the laser beam is controlled in a position-dependent manner during the laser cutting so that differences in material thicknesses can be better taken into consideration.

The processing time during the laser cutting is advantageously less than 2 s, preferably about 1 s.

It is also advantageous for an increased capillary action when the boundary edges of the longitudinal slot are formed with an edge angle of less than 100° and preferably about 90°.

Another advantageous procedure provides that a sharp lancing member is produced by grinding on the sampling element so that the lancing member is delimited by at least one flat grinding. In this connection it is also advantageous when a wire or a flat tape is machined as the starting material.

BRIEF DESCRIPTION OF THE DRAWINGS

The invention is elucidated in more detail in the following on the basis of the embodiment examples shown schematically in the drawing.

DESCRIPTION OF THE SELECTED EMBODIMENTS

Figure 1:
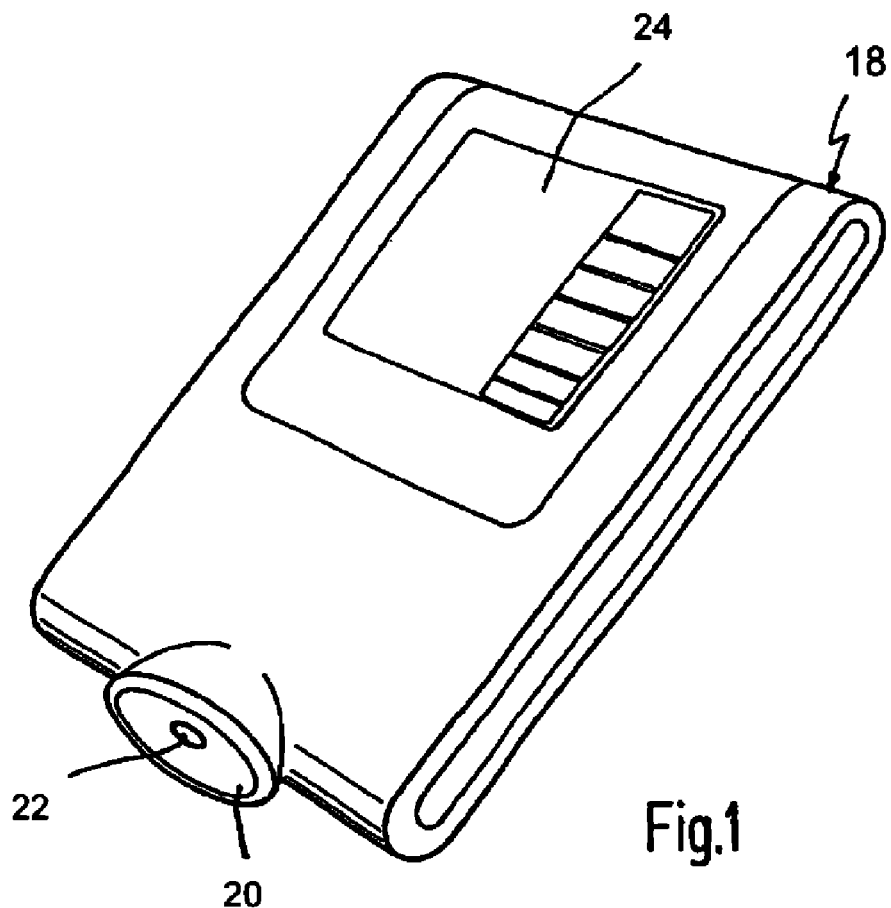
FIG. 1 shows a handheld device for blood sugar measurement in a perspective view.

The assembly 1 shown in the diagram comprises at least one sampling element 10 with a collecting area in the form of a longitudinal slot 12 for collecting body fluid obtained from a body part 14 at a puncture site and a sample receiving element 16 which can be brought into fluidic contact with the longitudinal slot for the blood sugar detection.

FIG. 1 shows a portable blood sugar measuring instrument 18 for the use of such a measuring assembly 1 for so-called "spot-monitoring" i.e. the self determination of the blood sugar concentration at a given time by a test person. For this purpose the instrument 18 has an inwardly conical support 20 for positioning the finger over a piercing opening 22 for the sampling or lancing element 10. The individual components of the instrument are activated in a fully automated measuring process so that in conjunction with a preferably disposable assembly 1 which is inserted into the instrument, the user ultimately obtains a measurement of his current blood glucose level on a display 24 without requiring a complicated handling. In general such a system can also be used to carry out measurements on other body parts such as the less pain-sensitive arm or stomach region, where in addition to capillary blood from the skin, tissue fluid or mixtures thereof are also suitable as a body fluid for the sample collection.

Figure 2:
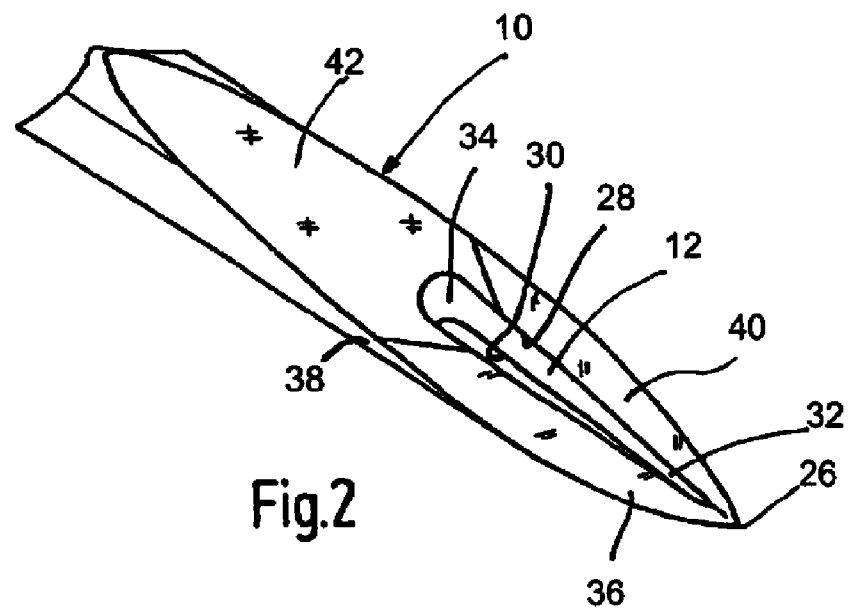
FIG. 2 shows a lancing element with a longitudinal slot for blood collection in a perspective view.

As shown in FIG. 2 the longitudinal slot 12 extends in the longitudinal direction of the shaft-like lancing element 10, for example over a length of 1 to 2 mm with a width of 100 to 200 µm. The distance from a tip 26 forming the lancing member can correspond to approximately the slot width. In this manner a capillary receiver is formed into which the body fluid that is made available by lancing the body part 14 (FIG. 4) flows in automatically due to capillary action.

Liquid is taken up on both sides via the opposing side openings 28, 30 of the longitudinal slot 12. In this connection the slot length in the lancing direction is such that a distal slot section 32 protrudes into the skin of the body part 14 and a proximal slot section 34 is located outside the skin. In order to reduce pain, the distal shaft section 36 which engages in the body can be designed to be "thin" i.e. have a tapered cross-section whereas the proximal shaft section 38 which remains outside the body has a widened cross-section compared thereto or a comparatively larger thickness in order to collect a sufficient amount of liquid. For example the amount of liquid corresponding to the slot volume can be 10 to 20 nanolitres where the partial volume of the longitudinal slot 12 located in the body for example has a volume percentage of 20%.

During the manufacture of such lancing elements 10, a wire as a starting material is firstly machined in a defined alignment by grinding processes to generate the differently angled ground surfaces 40, 42. Then the longitudinal slot 12 is introduced into this surface structure expediently in the same processing station while maintaining the rotary alignment using a suitably positioned laser. An important production detail is that the laser energy and/or the speed of movement of the laser beam is controlled as a function of the cutting position; this allows tapered openings to be shaped and it also allows a compensation for different material thicknesses.

Only a few movements of the laser beam are necessary for the slot opening and the processing time can be kept sufficiently short for mass production for example in the range of 1 sec. The mechanical tolerances can also be kept small for example in the range of 10 μm and wall slopes of almost 90° are achievable. Furthermore, activated and/or hydrophilic surfaces can be created for a coating by suitable laser treatment in particular under protective gases or special gases, said surfaces can optionally be further improved by a physical or wet-chemical after-treatment.

The lancets 10 produced in this manner can be inserted in an orientated manner into a plastic holder. The holder can for example come from a roll and the connection with the lancet can take place in a positionally correct manner by clipping, heat deformation etc. The plastic holder can have a coupling piece so that the lancets can engage and move within the instrument 18.

Figure 3:
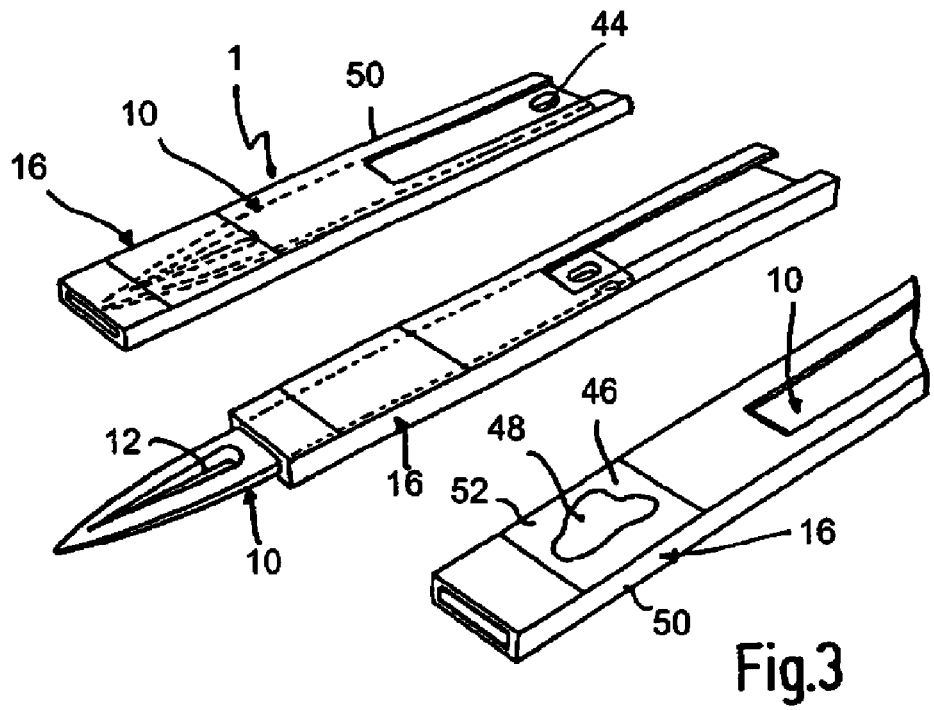
FIG. 3 shows an integrated measuring arrangement comprising a lancing element and test element in various process steps in a perspective view.

FIG. 3 shows a unit consisting of sampling element (lancing element 10) and sample receiving element 16. The sample is taken by a reciprocating lancing movement of the lancing element 10, where a suitable drive is coupled in a form-fitting manner to the proximal shaft part 44. The sample receiving element 16 which is held in a fixed position in the instrument during the lancing process is part of a sliding guide in the form of a holder for the lancing element 10 and has a test field 46 for receiving the body fluid 48 that previously collected in the longitudinal slot 12. Hence the holder that acts as a linear guide encloses the lancing element in a rectangular-flat configuration in which the broad sides face the side openings 28, 30 of the longitudinal slot 12. In addition to an advantageous liquid transfer, this also ensures a protection of the lancing element 10 and a hygienic disposal.

Thus the lancing element 10 fulfils a feeder function as a "shuttle" during sample collection whereas the actual detection of the analyte takes place on the sample receiving element 16 which does not come into contact with the body part 14. This element can also be provided as a component of a magazine comprising a plurality of divided compartments 50 which can be inserted into the instrument 18 as a consumable and can be disposed of together with the used lancing elements. The detection of glucose on the test field or reagent carrier 46 can be carried out photometrically by reflection through the transparent cover window 52 so that the blood fluid 48 in the compartment 50 remains hygienically separated from the instrument parts. Other detection techniques are also conceivable for example by fluorescence or electrochemical detection.

Figure 4:
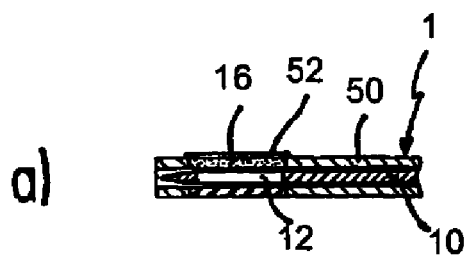
FIG. 4 shows a measuring process corresponding to FIG. 3 in an axial section.
Figure 4:
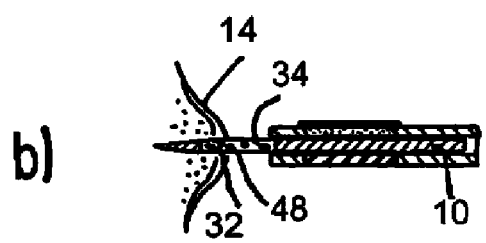
Figure 4:
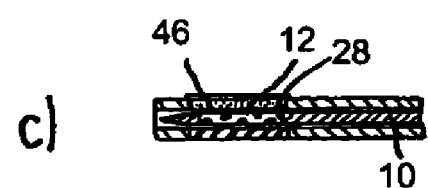
Figure 4:
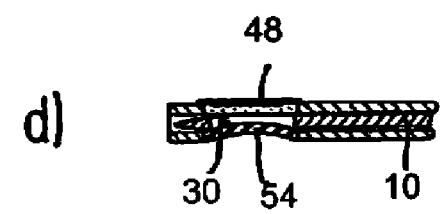

The essential steps of sample transfer are again illustrated in more detail in FIG. 4. In the initial position (4a) the lancing element 10 is protected in the magazine compartment 50 the front side of which can be sealed by a piercable foil. The lancing movement into the body part 14 (for example a finger tip) takes place as rapidly as possible and in an optimized movement because of the pain, and it is also possible to optionally steer toward a collecting position that is slightly retracted from the maximum puncture depth. The distal slot section 32 advantageously extends into the inside of the skin for the collecting process according to (4b) while the proximal slot section 34 fulfils a venting function outside the skin. This allows the blood fluid collected in the lancing channel to flow into the collecting slot 12 on both sides within a short collecting period and to efficiently fill the entire slot volume. In the collecting position the slot 12 is spatially separated from the sample receiving element 16 in such a manner that there is no fluidic connection between them and the detection reagents cannot reach the inside of the body. This also allows the detection process to be started specifically and allows the measurement time-course to be evaluated as such. For this purpose the lancing element 10 is pulled back again as shown in FIG. 4c) until the upper side opening 28 of the slot 12 is under the test field 46. The test field can for example due to a fleece structure have a larger capillary attractivity than the slot 12 in order to automatically transfer the collected blood. However, the liquid transfer is preferably assisted by pushing in a membrane 54 at the lower slot opening 30 as a displacement means for the collected fluid, as shown in FIG. 4d). Hence, fluid is transferred over the entire slot length over a short distance transversely to the lancing direction of the lancing element 10.

Figure 5:
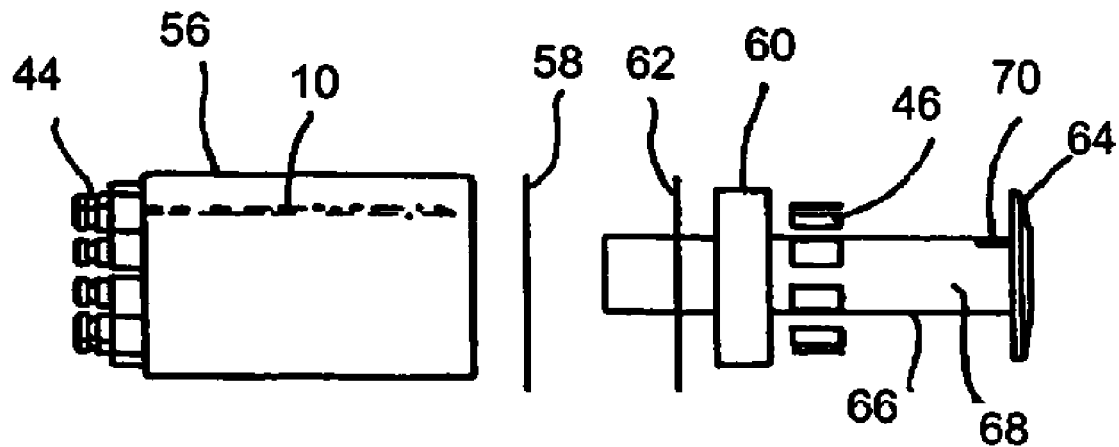
FIG. 5 shows a magazine for a blood sugar measuring instrument in an exploded diagram.
Figure 7:
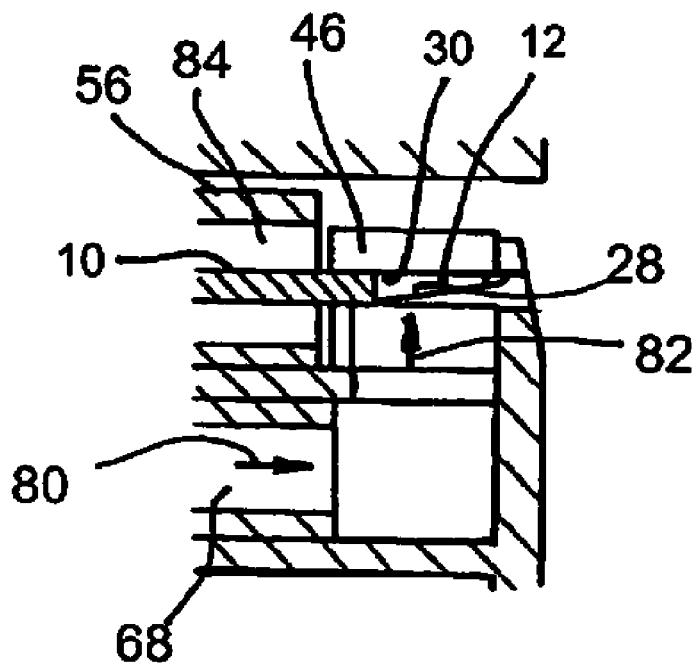
FIG. 7 shows an enlargement of a section of FIG. 6c.

The embodiment shown in FIGS. 5 to 7 also realizes this principle in which a special magazine storage and actuation are provided. According to FIG. 5 the lancing elements 10 are stored in a lancet drum 56 from the rear end face of which coupling pieces 44 project for the drive coupling whereas the front (distal) end face is sealed by a piercable foil 58. A separate test strip drum 60 can be loaded with test strips 46 by means of a slide-in slot which are then screened by a foil 62 and a front cap 64 from the environment and in particular from entry of moisture. The front cap 64 sits on a hollow spindle of the drum 66 which also forms an air passage 68 for a pneumatic actuation through the blow opening 70 on the casing. The separate storage in magazines enables different requirements to be taken into consideration. The lancing elements 10 which come into contact with the body can be advantageously sterilized in the lancet drum 56 by energy-rich radiation while independently thereof the radiation-sensitive test chemistry remains protected from external influences in the test strip drum 60 and also does not come into contact with the body during the lancing process.

Figure 6A:
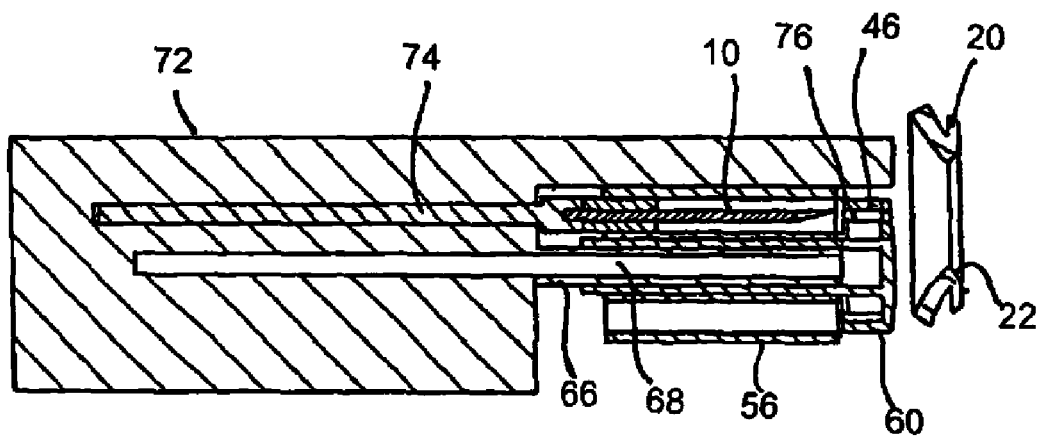
FIG. 6 shows the measuring process when the magazine according to FIG. 5 is used in a longitudinal section.
Figure 6B:
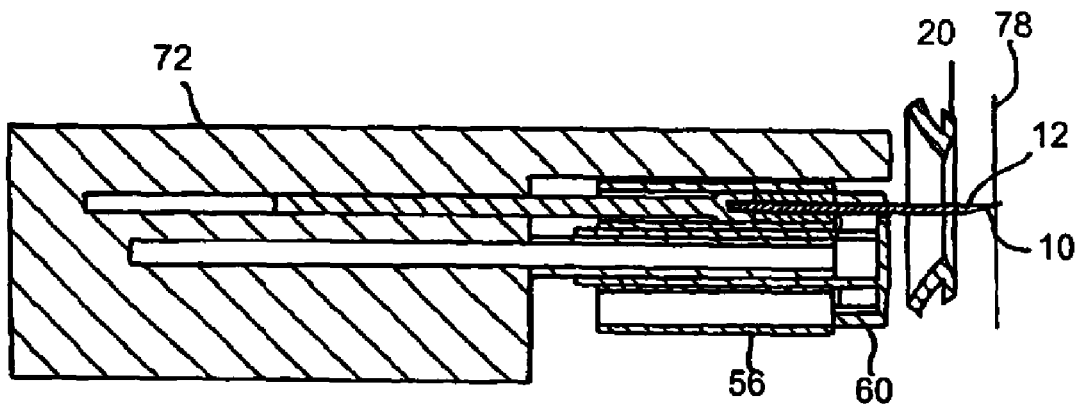
Figure 6C:
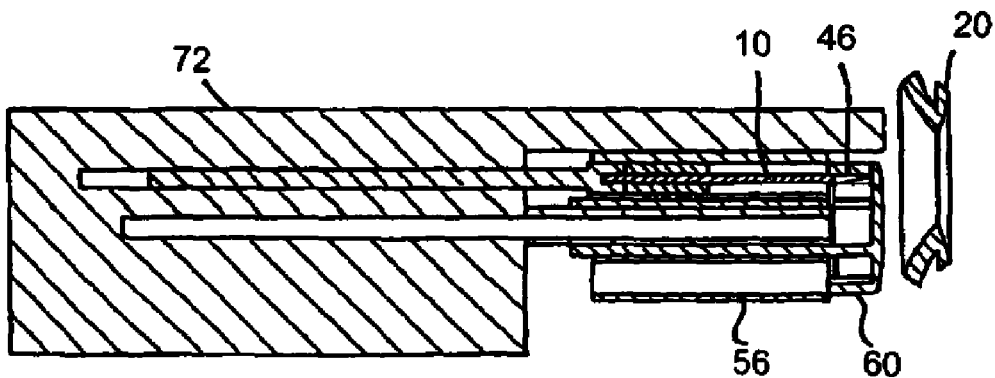

As shown in FIG. 6, the magazines 56, 60 are axially coupled on the drum axis 66 in the assembled state so that in each case one lancing element 10 and one test strip 46 are allocated to one another. A magazine receiver 72 within the instrument 18 enables compressed air to be applied to the air passage 68 and the lancing drive of the respective lancing element 10 that is coupled to a drive plunger 74 in coaxial alignment to the finger cone 20 (FIG. 6a). During the lancing propulsion the actuated lancing element 10 pushes through the chamber 76 of the associated test strip 46 located in front of it and reaches its maximum advance position through the cone opening 22 (line 78 in FIG. 6b) while travelling a distance of about 10 mm. Blood is then collected via the slot 12 as described above. Subsequently it is moved to the transfer position shown in FIG. 6c in the return movement of the lancing element 10 in which the slot 10 aligns in its outlet direction with the test strip 46.

As shown best in the enlarged section of FIG. 7 the collected fluid on the test strip 46 can be specifically transferred in the transfer position. For this purpose a blast of air is triggered through the air passage 68 in the direction of the arrows 80, 82 which impacts the facing side opening 28 of the slot 12 so that the blood fluid is displaced onto the test strip 46 through the opposing side opening 30 and is measured there. The glucose can then be detected reflectometrically by instrument optics that are not shown. Subsequently the contaminated lancing element 10 is completely retracted into the holding chamber 84 of the drum magazine 56 and the next function pair 10, 46 is made ready by rotating the drum.

The invention claimed is:

1. Assembly for receiving body fluids comprising a sampling element which is provided with a lancing member for insertion into a body part and has a collecting area for collecting body fluid obtained by a puncture, wherein the collecting area is formed by a longitudinal slot which is elongated as a capillary and is open on both sides via side openings on the sampling element, wherein the lancing member has a distal end that is closed, and comprising a sample receiving element to which body fluid can be applied via the collecting area and provided with a test field for an analyte in the body fluid, wherein the longitudinal slot is separated from the sample receiving element in a collecting position of the sampling element and is in fluidic contact with the sample receiving element in a transfer position of the sampling element, and wherein a distance between the test field and the sampling element varies between the collecting position and the transfer position.

2. Assembly according to claim 1, characterized in that the length of the longitudinal slot is such that the longitudinal slot is partially within and partially outside the body part in the collecting position of the sampling element.

3. Assembly according to claim 1, characterized in that the longitudinal slot has a distal receiving section protruding into the skin of the body part and a proximal venting section located outside the skin when the body fluid is collected.

4. Assembly according to claim 1, characterized in that the longitudinal slot has a length of 0.5 to 4 mm and a width of less than 500 μm.

5. Assembly according to claim 1, characterized in that the longitudinal slot is arranged at a distance of about 50 to 200 μm from a distal tip of the sampling element which forms the lancing member.

6. Assembly according to claim 1, characterized in that the sampling element has a distal shaft section with a tapered cross-section in the area of the longitudinal slot and a proximal shaft section with a widened cross-section.

7. Assembly according to claim 1, characterized in that a side opening as an outlet of the longitudinal slot can be brought into fluidic contact with the sample receiving element.

8. Assembly according to claim 1, characterized in that a side opening of the longitudinal slot is connected in the transfer position to an actuator in order to transfer body fluid onto the sample receiving element.

9. Assembly according to claim 8, characterized in that the actuator acts on the body fluid in the longitudinal slot by pneumatic displacement.

10. Assembly according to claim 8, characterized in that the actuator is formed by a membrane that can be deformed against the longitudinal slot.

11. Assembly according to claim 8, characterized in that the actuator has a passage for compressed air that can be coupled to a side opening of the longitudinal slot.

12. Assembly according to claim 1, characterized in that the sample receiving element has a larger capillary attraction for the body fluid than the longitudinal slot.

13. Assembly according to claim 1, characterized in that the sampling element is movably mounted in a guide relative to the sample receiving element.

14. Assembly according to claim 1, characterized in that the sample receiving element forms a case which receives the sampling element.

15. Assembly according to claim 1, characterized in that several sampling elements are stored in a first magazine and several sample receiving elements are stored in a second magazine, wherein the magazines as separate units can be connected together in order to couple the sampling elements and sample receiving elements in pairs.

16. Assembly according to claim 1, characterized in that a plurality of sampling elements are arranged in a magazine such that they can be ejected axially and that their associated sample receiving elements preferably arranged in push-through chambers are arranged in front of the magazine in the direction of ejection.

17. Portable blood analyser for receiving at least one assembly according to claim 1 preferably in the form of a single-use article.

18. System for analysing body fluids comprising a sampling element which is provided with a lancing member for insertion into a body part and has a longitudinal slot elongated as a capillary that is open on both sides via side openings as a collecting area for collecting body fluid obtained by a puncture at a collecting position, wherein the lancing member has a distal end that is closed, and a sample receiving element to which body fluid can be applied via the collecting area at a transfer position, wherein the sample receiving element is provided with a test field for an analyte in the body fluid, wherein an actuator is provided for transferring body fluid from the sampling element onto the sample receiving element when the sample receiving element is at the transfer position, and wherein a distance between the test field and the sampling element varies between the collecting position and the transfer position.

19. System according to claim 18, characterized in that the actuator acts from a side opening on the body fluid in the longitudinal slot and that an analyte in the body fluid is measured on the opposing side of the sampling element.

20. System according to claim 19, characterized in that in a transfer position, the sampling element is in fluidic contact with the sample receiving element via the side opening facing away from the actuator.

21. System according to claim 18, characterized in that a preferably optical measuring unit is provided to detect an analyte on the test field to which body fluid has been applied.

22. Assembly according to claim 1, characterized in that the longitudinal slot has a length of 1 to 2 mm and a width of less than 100 μm.

23. Assembly according to claim 8, characterized in that the actuator acts on the body fluid in the longitudinal slot by mechanical displacement.

24. Assembly according to claim 16, wherein the magazine is a drum magazine.

25. An assembly, comprising:
a sample receiving element having a test field;
a lancing element guided by the sample receiving element, the lancing element having a slot with opposing side openings for collecting body fluid, wherein the lancing member has a distal end that is closed;
the slot of the lancing element being moveable relative to the sample receiving element from a collecting position to a transfer position;
at the collecting position the slot of the lancing element is extended from the sample receiving element for collecting the body fluid in the slot and the slot is unable to transfer the body fluid to the test field; and
at the transfer position the slot of the lancing element is aligned with the test field and is able to transfer the body fluid from the slot to the test field.

26. The assembly of claim 25, further comprising:
a displacement mechanism configured move the body fluid from the slot to the test field when the slot is at the transfer position.

27. The assembly of claim 26, in which the displacement mechanism includes a membrane located opposite the test field for pushing the body fluid from the slot onto the test field when the slot of the lancing element is located at the transfer position.

28. The assembly of claim 26 in which the displacement mechanism includes an air passage located opposite the test field for directing a blast of air that blows the body fluid from the slot onto the test field when the slot of the lancing element is located at the transfer position.

29. The assembly of claim 26, further comprising:

wherein the lancing element moves in a longitudinal direction when moving from the collecting position to the transfer position; and wherein the displacement mechanism is configured to move the body fluid from the slot to the test field in a transverse direction relative to the longitudinal direction.

30. The assembly of claim 25, in which the test field has greater capillary affinity than the slot to promote transfer of the body fluid from the slot to the test field.

31. The assembly of claim 25, wherein the sample receiving element has a broad side that faces the opposing side openings when at the transfer position to facilitate transfer of the body fluid.

* * * * *